United States Patent [19]

Carpenter et al.

[11] Patent Number: 5,254,861
[45] Date of Patent: Oct. 19, 1993

[54] BIOLOGICAL AEROSOL PARTICLE DETECTOR AND METHOD HAVING AN ELECTRONIC PULSE DETECTION MEANS

[75] Inventors: David R. Carpenter, Austin; John Taboada, San Antonio, both of Tex.

[73] Assignee: The United States of America as represented by the Secretary of the Air Force, Wright-Patterson Air Force Base, Ohio

[21] Appl. No.: 953,638

[22] Filed: Sep. 29, 1992

[51] Int. Cl.$^5$ ............................................. G01N 15/06
[52] U.S. Cl. ................................... 250/573; 250/379; 324/464
[58] Field of Search ............ 250/573, 574, 379, 423 P; 356/338; 324/464, 465, 466, 71.1, 71.2, 71.3, 71.4

[56] References Cited

U.S. PATENT DOCUMENTS

| | | | |
|---|---|---|---|
| 3,932,851 | 1/1976 | Rayl et al. | 340/237 S |
| 3,967,931 | 7/1976 | Juvet, Jr. et al. | 23/230 PC |
| 4,134,111 | 1/1979 | Nudds | 340/629 |
| 4,429,228 | 1/1984 | Anderson | 250/374 |
| 4,837,440 | 6/1989 | Burtscher et al. | 250/379 |
| 5,153,519 | 10/1992 | Wentworth et al. | 324/464 |

OTHER PUBLICATIONS

"Photoelectric Charging and Detection of Ultrafine Particles", Federer et al, Atmospheric Environment 17:3, 655–657 (1983).
"The Chemical Response of the Photo-Electric Aerosol Sensor (PAS) to Different Aerosol Systems", Niessner, J Aerosol Sci 17, 704–714 (1986).
*Aerosol Technology*, Hinds, John Wiley & Sons, New York (1982).

*Primary Examiner*—David C. Nelms
*Assistant Examiner*—Que T. Le
*Attorney, Agent, or Firm*—Bobby D. Scearce; Thomas L. Kundert

[57] ABSTRACT

System and method for detection and measurement of airborne biological aerosol particles in a gaseous sample are described comprising a source of low energy radiation for irradiating the gaseous sample whereby biological particles in the sample are ionized, a detector for detecting ionized biological particles in the sample including a pair of electrically charged conducting plates disposed in parallel confronting relationship to each other with a preselected space therebetween, a source of electrical power operatively connected to the plates for applying a preselected electrical potential thereacross, and electronics for sensing collisions on the plates of ionized biological particles in the sample.

28 Claims, 2 Drawing Sheets

BIOLOGICAL AEROSOL PARTICLE DETECTOR AND METHOD HAVING AN ELECTRONIC PULSE DETECTION MEANS

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems and methods for airborne particle detection, and more particularly to system and method for detection of biological aerosol particles.

In the prior art, detection of biological aerosol particles typically comprises particle impingement on auger plates followed by examination of the plates by a trained mycologist or bacteriologist for determination of contamination levels. This procedure normally requires about two weeks for laboratory testing and is substantially affected by the type of auger used, growth media, time between sampling and analysis, storage/shipment conditions, and other factors. Measurement of total biological aerosol level requires several different augers to grow the various biological materials. The procedure has substantial variability in accuracy of analyses by the same laboratory on samples taken at the same location and time (typically up to 3 orders of magnitude in reported biological concentration), and, therefore, multiple samples are required to obtain statistically useful data.

The prior art systems for detecting biological aerosol particles measure flow of electrical current through an air sample, include sensitive electrometers to measure current, are slow and require a large concentration of biological particles per unit volume of sample, and are therefore not adequate for measuring low concentrations or any field environment monitoring.

The invention solves or substantially reduces in critical importance problems in the prior art as just stated by providing system and method for detection and concentration measurement of airborne biological aerosols, wherein a sample air flow is passed through a soft ultraviolet ionizing chamber and exposed to ionizing energies of less than about 7.5 eV. Charged biological particles in the flow are distinguishable from less readily chargeable non-biological particles. Biological aerosols are detectable discriminately as single particles in dusty environments.

The invention may be used for detecting spores, fungi, algae, pollen, bacteria, organic dusts and some viruses at single particle to high concentration levels, and finds particular utility for monitoring areas sensitive to airborne biological materials, such as clean rooms, surgical suites, hospitals and food preparation areas, or for detecting biological warfare agents. The invention provides the only known system and method for real time assessment of infectious biological aerosols such as legionella.

It is a principal object of the invention to provide system and method for detecting airborne biological particles.

It is a further object of the invention to provide real-time particle detection method and system for biological aerosols.

These and other objects of the invention will become apparent as a detailed description of representative embodiments proceeds.

SUMMARY OF THE INVENTION

In accordance with the foregoing principles and objects of the invention, system and method for detection and measurement of airborne biological aerosol particles in a gaseous sample are described comprising a source of low energy radiation for irradiating the gaseous sample whereby biological particles in the sample are ionized, a detector for detecting ionized biological particles in the sample including a pair of electrically charged conducting plates disposed in parallel confronting relationship to each other with a preselected space therebetween, a source of electrical power operatively connected to the plates for applying a preselected electrical potential thereacross, and electronics for sensing collisions on the plates of ionized biological particles in the sample.

DESCRIPTION OF THE DRAWINGS

The invention will be more clearly understood from the following detailed description of representative embodiments thereof read in conjunction with the accompanying drawings wherein:

FIGS. 2b, 2c, and 2d illustrate the conditions experienced by a charged particle upon collision with the plates of FIG. 2a.

DETAILED DESCRIPTION

Figure 1:
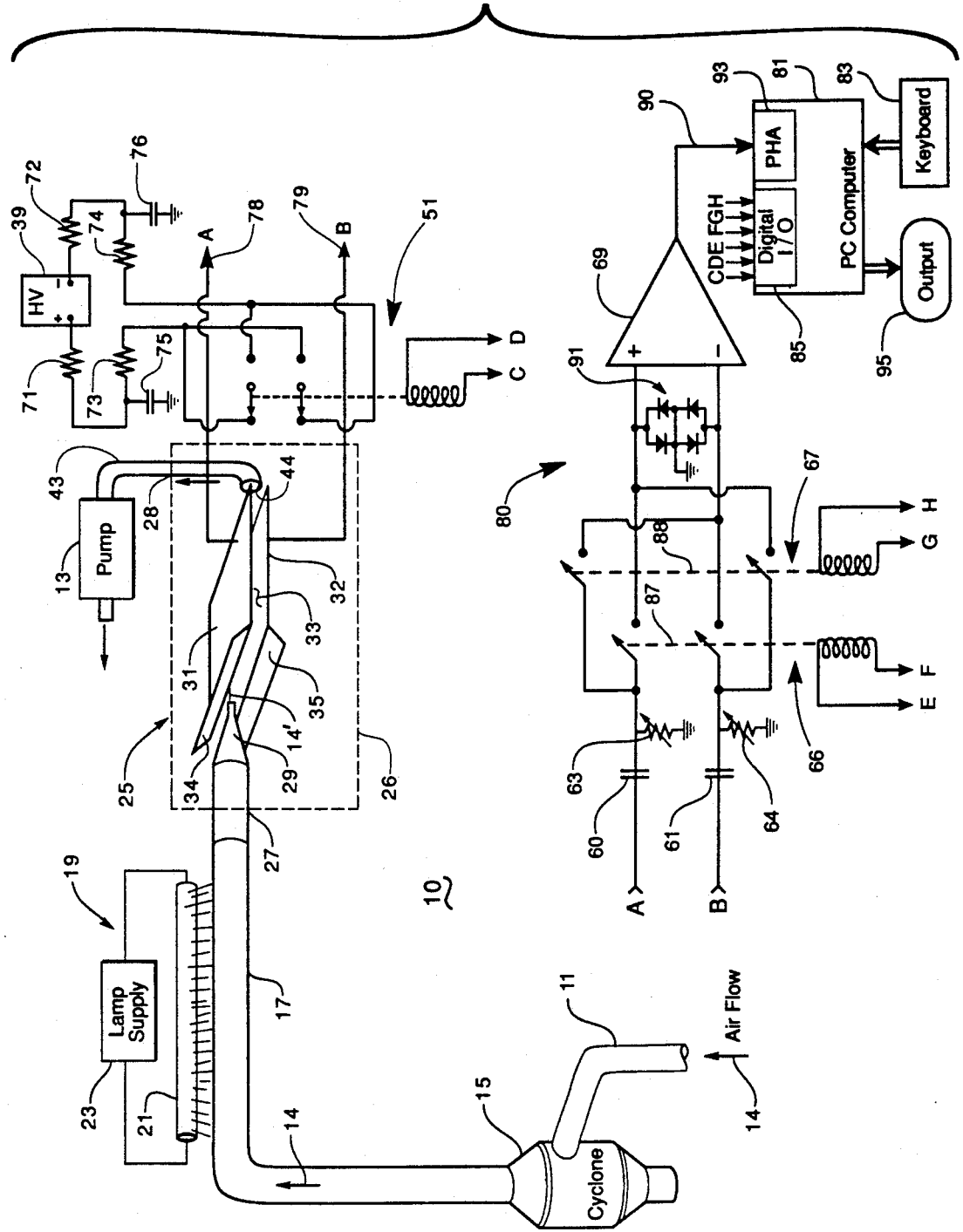
FIG. 1 is an overall schematic of essential components and circuitry of a biological aerosol particle detector of the present invention.

Referring now to the drawings, FIG. 1 is a schematic of the essential components and electronic circuitry of biological aerosol particle detection system 10 representative of the invention. Air sampling means, such as air inlet tube 11, provide an ambient sample for examination. A substantially conventional pump 13 of selected pumping rate (about 1-10 liters/min) is disposed to aspirate flow 14 of sampled air through system 10 as described below. In a system built in demonstration of the invention, pump 13 (model Alpha-1, Dupont Company) provided flow 14 of sample air at a nominal rate of 2 liters/min. It is preferable first to remove large inorganic particles from sample flow 14 by directing it through means in the form of cyclone 15, filter or the like. In the demonstration system, a standard cyclone (model SKC-225-0101, SKC Gulf Coast Company, Inc.) was used which admits small particles (100% at $\leq 1\mu$, 50% at about $5\mu$, 0% at $10\mu$), and prevents larger particles from entering the system. Flow 14 then passes through tube 17 which comprises a material which is transparent to ultraviolet (UV) radiation (such as quartz or sapphire). An intense UV radiation source 19 including lamp 21 and power source 23 is disposed near tube 17 for irradiating flow 14 at low energy to ionize biological aerosols carried therewith. In the effective operation of the invention, lamp 21 may typically radiate at about 200 to 300 nanometers (nm) in order to provide a desired degree of ionization to the biological aerosols carried by flow 14, and may comprise a mercury vapor lamp (250 nm) as in the demonstration system or xenon (308 nm), argon (370 nm), cadmium (442 nm) or other UV source of desired wavelength. Radiation from the mercury vapor lamp has associated photon energy of about 4.9 eV, although other usable UV sources may have somewhat larger or smaller associated photon energies (about 2.8 to 7.5 eV). The UV photons from lamp 21 interact with the electronic structures of the substances comprising the biological aerosol particles carried by flow 14. Many substances found in biological aerosols have a work function less than 4.9 eV, and collisions of the UV photon with outer shell electrons of these substances result in the removal of electrons from the outer shells and in a net positive charge on the aerosol particle.

Immediately downstream of UV source 19 is disposed a particle detector 25 of novel configuration for detecting charged aerosol particles within flow 14. Detector 25 includes a substantially sealed housing 26 having an inlet 27 and an outlet 28. Inlet 27 is connected to and communicates with tube 17, and defines nozzle 29 in a terminal end of tube 17 for confining flow 14 as a fine stream 14'. Nozzle 29 is preferably sized in cross section to maintain a laminar flow in stream 14', which implies a flow velocity normally of about 0.5 to 2 meters/sec, and typically about 1 meter/sec for cross sections of a few square mm. Detector 25 comprises a pair of charged parallel conducting plates 31,32 having preselected spacing 33 therebetween and between which stream 14' carrying charged biological aerosol particles is injected. In the demonstration system, plates 31,32 were polished aluminum metal, 45 mm long by 38 mm wide with 1.6 mm spacing. Plates 31,32 may comprise other materials and may be otherwise sized and spaced for a given application within the contemplation of the invention and scope of the appended claims. The ends of plates 31,32 confronting nozzle 29 are flared as at 34,35 to facilitate flow of stream 14' and to avoid edge effects at the point of injection of stream 14'. Adjustable high volta DC power source 39 (typically about 210 kilovolts maximum) is connected across plates 31,32 to provide suitable charging potential in the range of about 0.5 to 10 kilovolts and preferably about 1 to 2 kilovolts. Tube 43 has inlet 44 disposed near the distal ends of plates 31,32 and is connected to outlet 28 operatively connected to pump 13 to provide means as suggested above to draw sample flow 14 and stream 14' through spacing 33 in the operation of the invention as described more fully below.

Figure 2A:
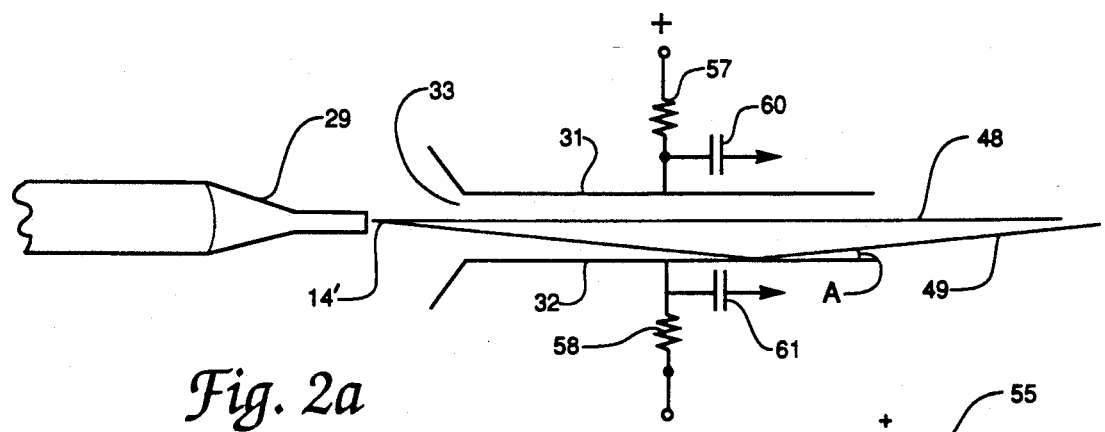
FIG. 2a is a diagram of the charged plates and charged particle detection region of the invention.

Referring now to FIG. 2a, shown therein is a schematic side view of nozzle 29 and plates 31,32 illustrating the path of charged biological aerosol particles carried by stream 14' along spacing 33 and influenced by the charging potential of lamp 21 FIG. 1). Upon injection into spacing 33, aerosol particles within 14', after interaction with UV radiation at source 19, will follow one of two trajectories 48,49. Uncharged particles will follow trajectory 48 and pass through the system without detection. Particles (positively) charged by UV irradiation are attracted to negative conducting plate 32.

As charged particles traverse the length l of spacing 33 between plates 31,32, the particle average dwell time t (sec) is, $$t = l/v \tag{1}$$

where v is the flow velocity of stream 14'. The particle average transverse drift velocity $v_t$ resulting in contact of the particle with a plate is, $$v_t = (d/2)/\text{dwell time} = d/2t = dv/2l \tag{2}$$

where d is the spacing between plates.

In the demonstration system (d=1.6 mm; l=45 mm; v=1 m/sec) $v_t$ equals 0.018 m/sec. Because the longitudinal velocity is much greater than the transverse drift, particle contact with a plate is a glancing collision at an incident angle A equal to $\tan^{-1}$ (0.018) or 0.02°. Because of the glancing collision, the charged particles have reduced tendency to stick to plates 31,32, but particle accumulation thereon may be avoided by applying a reversing field applied to plates 31,32 using relay 51 (FIG. 1) which is a high voltage double pole double throw relay (e.g., Kilovac model H-18).

In order for a charged particle to drift to plates 31,32, a frictional drag force $f_f$ given by the Navier Stokes relationship must be overcome, viz., $$f_f = 6\pi r n (dx/dt) \tag{3}$$

where r is the particle radius (about 1 82 m), n is viscocity of air ($4 \times 10^{-8}$), and dx/dt is the transverse velocity calculated above to be about 0.018 m/sec. The resulting force $f_f$ is $1.4 \times 10^{-14}$ newtons. The coulomb force $f_c$ (newtons) is, $$f_c = NqE \tag{4}$$

where N is the number of charges per particle, q is the electron charge and E is the electric field strength (volts/meter). In the limit of one charge (N=1), the required field to obtain a particle detection is determined by equating the frictional force to the coulomb force, obtaining, $$E = 6\pi r n (dx/dt)/q = 87.4 \text{ kV/meter}. \tag{5}$$

The required applied potential to plates 31,32 is of the order of 100 kV/meter. The charge transfer dq by the particle required to obtain measurable electrical response at 1 microvolt is, $$dq = cdv \tag{6}$$

where c is the capacitance of the sensor plate and dv is the voltage detection limit value ($\sim 1 \times 10^{-6}$ volts).

In the demonstration system, the capacitance of the sensor plate was 9.5 picofarads. From Eq (6), dq is, $$\begin{aligned} dq &= (9.5 \times 10^{-12})(1 \times 10^{-6}) \text{ volts} \\ &= 9.5 \times 10^{-18} \text{ coulombs} = 59 \text{ electron charges}. \end{aligned} \tag{7}$$

Figure 2B:
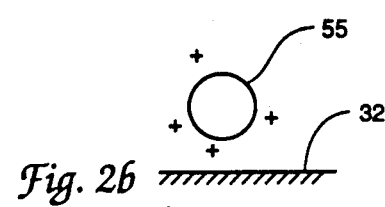
Figure 2C:
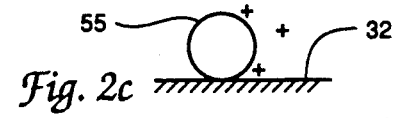

Since the total charge sites on a typical biological particle are of the order of $10^5$, only a small efficiency in charging the particle by the ionizer is required. Upon colliding with plates 31,32, charged particle 55 experiences conditions shown in FIGS. 2b,c,d. As illustrated in FIG. 2b, particle 55 charged by lamp 21 may have a plurality of positive charges. Collision of particle 55 with plate 31 or 32 results in a number of negative charges flowing from the high voltage pole of power source 39 to the negative plate 31,32 to particle 55. The current path requires the charge to flow through a resistors 57 and 58 to neutralize the charge on particle 55. The momentary charge cancellation on the plate creates a momentary electrical pulse with amplitude dv:

$$dv = dq/c \qquad (8)$$

Figure 2D:
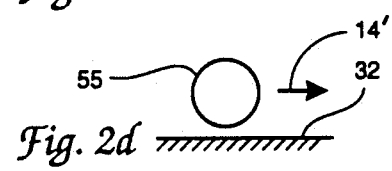

This voltage pulse is coupled by capacitors 60,61. Referring now to FIG. 1, the respective signal pulse is induced across adjustable resistors 63,64. These induced signals are connected by either relay 66 or 67 to a high gain ($10^3$) low noise (0.3 microvolt) instrumentation amplifier 69 (e.g., Analog devices model AD624). After charge cancellation as just described, the then substantially neutral particle 55 flows out of the system with stream 14' as suggested in FIG. 2d.

Still referring to FIG. 1, the noise generated by the DC-DC conversion process in source 39 and imposed on plates 31,32 is electronically filtered by circuitry including resistors 71–74 and capacitors 75,76, to eliminate or substantially reduce voltage ripple noise to less than 10 microvolts. Signals 78,79 generated by charge transfer in the collision of particles on plates 31,32 are coupled to signal amplification system 80.

Computer 81 (e.g. IBM PC, AT or XT), through software and suitable hardware such as keyboard 83, controls the sequencing of activation of relays 51,66,67. The communication for activation of the relays is accomplished by digital I/O board 85 (Industrial Computer model 5610 Reed Relay Card). The computer sequentially actuates relays 51 then 66 or 67. Relay 51 is switched to one or the other pole pairs. Plates 31,32 are charged to a given polarity after the transients are passed, then relay 66 or 67 actuates contact 87 or 88 to connect signals 78 and 79 to amplifier 69. The sequence of relay actuation achieves two ends, relay 51 alternates the field on the plate to reduce particle collection and relays 66 and 67 maintain a disconnected state while the field is reversed to protect the sensitive amplifiers from transients. Relays 66 and 67 are sequenced to permit the amplifier to track polarity of plates 31,32 and keep the signal positive at 90. Diode array 91 also adds protection against transients.

Signal 90 may be processed by a conventional pulse height analyzer 93 which sorts pulse events into a range distribution of heights related to the charge transfer by the particles. Since the particles are restricted to a given predominant size by cyclone 15, pulse height distribution is related to the mobility of the particles. This characterization can sort the biological particles into various classes such as spores, bacteria or inorganic particles. The computer outputs the pulse height analyzer results onto output 95 (numerical display, CRT, printer, data logger, alarm, etc.).

Figure 3:
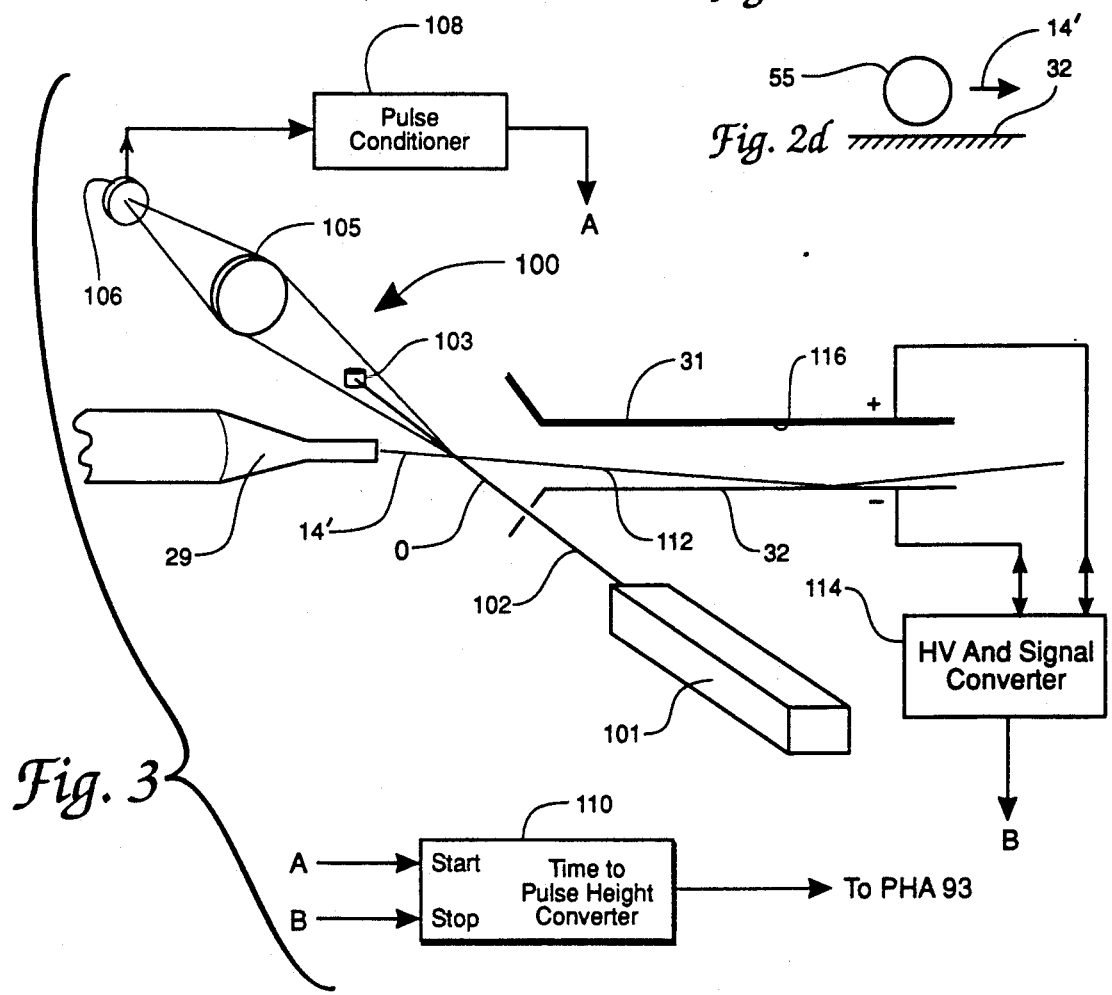
FIG. 3 is a diagram of an alternative structure incorporating a laser optical detection method to produce a more accurate mobility measurement or distinction of the aerosol particles.

Referring now to FIG. 3, shown therein is a detector structure 100 alternative to that of FIGS. 1, 2a. In structure 100, infrared laser diode 101 emits beam 102 (e.g., with wavelength of 800 nm which intersects stream 14' near nozzle 29. Beam stop 103 is disposed along optical axis 0 of beam 102 for terminating any undeflected portion thereof. Any portion of beam 102 which is intercepted and deflected by particles in stream 14' off axis 0 is focused by optics 105 onto high speed photodiode 106. The signal from photodiode 106 is amplified by signal conditioner 108 and serves as the start input signal A of a conventional time-to-pulse height converter 110. If a particle in stream 14' is sufficiently charged, it will traverse the spacing between plates 31,32 along a trajectory represented by 112 and is detected by high voltage and signal conditioning electronics 114 as particle impact pulse signal B substantially as described above in relation to FIGS. 1,2a. Signal B occurs a short time interval after signal A, the interval being a measure of the charge and drift velocity of the particle, i.e. mobility. The particles with the smallest dimension and highest charge have the shortest interval between signals A and B and may be identified as biological because of their propensity to ionize. The time interval between signals A,B may be measured using conventional time-to-pulse-height converter 110. Output of converter 110 is input to pulse height analyzer 93 (FIG. 1). The results are a pulse height system related to particle mobility. Alternatively, signals from photodiode 106 may be analyzed by using an additional pulse height analyzer such as 93 wherein the pulse interval and pulse height analysis of the charge exchange impact can be combined to form a 3-D cluster of points for monitoring aerosols. By having more dimensions characterizing the aerosol particle, an improvement in identification is achievable.

An additional feature of the FIG. 3 embodiment is the incorporation of a thin (a few microns) insulating layer 116 on one of plates 31,32. Layer 116 blocks interaction of one polarity of particles with the corresponding plate, thus simplifying counting statistics to one subgroup, for example the positively charged biological particles.

The invention therefore provides system and method for detection of biological aerosol particles. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

We claim:

1. A system for detecting airborne biological particles in a gaseous sample, comprising:
   (a) a source of low energy radiation;
   (b) means for flowing a gaseous sample past said radiation source for irradiating said sample with low energy radiation and thereby selectively ionizing biological particles in said sample;
   (c) a detector for detecting and characterizing ionized biological particles in said sample, said detector including a pair of electrically charged conducting plates disposed in parallel confronting relationship to each other with a preselected space therebetween;
   (d) a source of electrical potential operatively connected to said plates for applying a preselected electrical potential across said plates;
   (e) means for flowing said sample between said plates; and
   (f) electronic pulse detection means for sensing collisions on said charged plates by said ionized biological particles in said sample.

2. The system of claim 1 further comprising pulse height analysis means for characterizing the pulses resulting from the said collisions of said ionized biological particles with said plates.

3. The system of claim 1 wherein said source of low energy radiation comprises an ultraviolet source.

4. The system of claim 3 wherein the photon energy of said ultraviolet source is in the range of from 2.5 to 7.5 eV.

5. The system of claim 1 wherein said electrical potential is in the range of 1 to 2 kilovolts.

6. The system of claim 1 further comprising means for removing particulate matter larger than 10 micrometers from said sample prior to irradiation thereof.

7. A system for detecting airborne biological particles in a gaseous sample, comprising:
(a) a source of low energy radiation;
(b) means for flowing a gaseous sample past said radiation source for irradiating said sample with low energy radiation and thereby selectively ionizing biological particles in said sample;
(c) a detector for detecting ionized biological particles in said sample, said detector including a laser-photo detector combination and a pair of electrically charged conducting plates disposed in parallel confronting relationship to each other with a preselected space therebetween;
(d) a source of electrical potential operatively connected to said plates for applying a preselected electrical potential across said plates;
(e) means for flowing said sample through said laser-photo detector combination and thence between said plates;
(f) means for electrically registering the response of the laser-photo detector combination to the passage therethrough of said ionized biological particles; and
(g) electronic pulse detection means for sensing collisions on said charged plate by said ionized biological particles in said sample.

8. The system of claim 7 further comprising means for comparing the signals from said laser-photo detector combination and said electronic pulse detection means whereby said ionized biological particles may be characterized based on the time of flight between the laser-photo detector signal and the collisions on said charged plates and the magnitude of charge transfer by said ionized biological particles onto said plates.

9. The system of claim 7 further comprising pulse height analysis means for characterizing the pulses resulting from the said collisions of said ionized biological particles with said plates.

10. The system of claim 7 wherein said source of low energy radiation comprises an ultraviolet source.

11. The system of claim 10 wherein the photon energy of said ultraviolet source is in the range of from 2.5 to 7.5 eV.

12. The system of claim 7 further comprising an insulating layer on one of said plates to block the charge transfer of one polarity of said ionized biological particles.

13. The system of claim 7 wherein said electrical potential is in the range of 1 to 2 kilovolts.

14. The system of claim 7 further comprising means for removing particulate matter larger than 10 micrometers from said sample prior to irradiation thereof.

15. A method for detecting airborne biological particles in a gaseous sample, comprising the steps of:
(a) irradiating a gaseous sample with low energy radiation to selectively ionize biological particles in said sample;
(b) providing a detector for detecting ionized biological particles in said sample, said detector including a pair of electrically charged conducting plates disposed in parallel confronting relationship to each other with a preselected space therebetween;
(c) applying a preselected electrical potential across said plates;
(d) flowing said sample between said plates; and
(e) detecting electronic pulses resulting from collisions on said plates by ionized biological particles in said sample.

16. The method of claim 15 further comprising the step of analyzing and characterizing said electronic pulses resulting from collisions on said plates by said ionized biological particles.

17. The method of claim 15 wherein said source of low energy radiation comprises an ultraviolet source.

18. The method of claim 17 wherein the photon energy of said ultraviolet source is in the range of from 2.5 to 7.5 eV.

19. The method of claim 15 wherein said electrical potential is in the range of 0.5 to 10 kilovolts.

20. The method of claim 15 further comprising the step of removing particulate matter larger than 10 micrometers from said sample prior to irradiation thereof.

21. A method for detecting and characterizing airborne biological particles in a gaseous sample, comprising the steps of:
(a) irradiating a gaseous sample with low energy radiation to ionize biological particles in said sample;
(b) providing a laser-photo detector combination for detecting ionized biological particles in said sample;
(c) providing a particle detector for detecting said ionized biological particles, said particle detector including a pair of electrically charged conducting plates disposed in parallel confronting relationship to each other with a preselected space therebetween;
(d) applying a preselected electrical potential across said plates;
(e) flowing said sample through said laser-photo detector combination and thence between said plates; and
(f) comparing the signals from said laser-photo detector combination and said particle detector whereby said ionized biological particles may be characterized based on the time of flight between the laser-photo detector combination signal and the collision on said charged plates and the magnitude of charge transfer by said ionized biological particles onto said plates.

22. The method of claim 21 wherein one of said detector plates is covered with a thin insulating layer to block the charge transfer of one polarity of said ionized biological particles.

23. The method of claim 22 wherein said insulating layer is on the one of said plates other than the one to which positively charged said ionized biological particles are attracted.

24. The method of claim 21 further comprising the step of analyzing and characterizing said electronic pulses resulting from collisions on said plates by said ionized biological particles.

25. The method of claim 21 wherein said source of low energy radiation comprises an ultraviolet source.

26. The method of claim 25 wherein the photon energy of said ultraviolet source is in the range of from 2.5 to 7.5 eV.

27. The method of claim 21 wherein said electrical potential is in the range of 0.5 to 10 kilovolts.

28. The method of claim 21 further comprising the step of removing particulate matter larger than 10 micrometers from said sample prior to irradiation thereof.

* * * * *